United States Patent
Parent et al.

(10) Patent No.: US 10,406,017 B2
(45) Date of Patent: Sep. 10, 2019

(54) DEVICES FOR APPLYING TENSION TO A PATIENT SHOULDER AND ASSOCIATED INSTALLATION METHOD

(75) Inventors: Stefan Parent, Saint-Lambert (CA); Jean-Marc Mac-Thiong, Montreal (CA); Hubert LaBelle, Laval (CA); Mark Driscoll, Notre-Dame-de l'Ile-Perrot (CA)

(73) Assignee: Spinologics Inc., Montreal (CA)

( * ) Notice: Subject to any disclaimer, the term of this patent is extended or adjusted under 35 U.S.C. 154(b) by 1127 days.

(21) Appl. No.: 14/343,217

(22) PCT Filed: Sep. 7, 2012

(86) PCT No.: PCT/CA2012/000839
§ 371 (c)(1),
(2), (4) Date: Mar. 6, 2014

(87) PCT Pub. No.: WO2013/033831
PCT Pub. Date: Mar. 14, 2013

(65) Prior Publication Data
US 2014/0224262 A1 Aug. 14, 2014

Related U.S. Application Data

(60) Provisional application No. 61/531,670, filed on Sep. 7, 2011.

(51) Int. Cl.
*A61F 5/37* (2006.01)
*A61B 6/04* (2006.01)

(52) U.S. Cl.
CPC .......... *A61F 5/3776* (2013.01); *A61B 6/0421* (2013.01); *A61F 5/3784* (2013.01); *F04C 2270/0421* (2013.01)

(58) Field of Classification Search
CPC .... A61B 6/0421; A61F 5/3769; A61F 5/3776; A61F 5/3784; A61F 5/37; A61F 5/3723
(Continued)

(56) References Cited

U.S. PATENT DOCUMENTS 1,320,032 A 10/1919 Bailey
2,377,940 A 6/1945 Hughes
(Continued)

FOREIGN PATENT DOCUMENTS

CN 202223487 U 5/2012
EP 1013248 A1 6/2000

OTHER PUBLICATIONS

International Search Report for PCT/CA2012/000839, dated Jan. 4, 2013, 2 pages.

*Primary Examiner* — Ophelia A Hawthorne
*Assistant Examiner* — Caitlin A Carreiro
(74) *Attorney, Agent, or Firm* — Foley & Lardner LLP (57) ABSTRACT

A device comprises an arm cover to be positioned under the arm before being closed thereover, a shoulder strap to be positioned under the shoulder and adapted to wrap the shoulder when attached, over the shoulder, to the closed arm cover and a longitudinal strap to be fixed to the table opposite to the head. The longitudinal strap can apply tension on the shoulder strap when shortened. A method for installing a device on an immobilized patient comprising positioning an arm cover under the arm and a shoulder strap connected to the arm cover under the shoulder, closing the arm cover over the arm and attaching the shoulder strap, over the shoulder, to the closed arm cover, fixing an end of a longitudinal strap, connected to the arm cover, to the table opposite to the head and pulling on the longitudinal strap to apply tension on the shoulder strap.

23 Claims, 7 Drawing Sheets

(58) Field of Classification Search
USPC ..... 128/869–871, 873, 877–878, 872; 5/621, 5/623, 628
See application file for complete search history.

(56) References Cited

U.S. PATENT DOCUMENTS

| | | | | |
|---|---|---|---|---|
| 2,560,243 | A * | 7/1951 | Coletta | A61F 5/3746 |
| | | | | 602/4 |
| 2,649,856 | A | 8/1953 | Schmeri | |
| 2,813,527 | A | 11/1957 | Cook | |
| 3,046,982 | A | 7/1962 | Davis | |
| 3,496,934 | A * | 2/1970 | Anderson | A61F 5/0585 |
| | | | | 602/16 |
| 3,605,736 | A | 9/1971 | D'Amico | |
| 3,629,581 | A * | 12/1971 | Smith | A61B 6/04 |
| | | | | 378/209 |
| 3,797,483 | A | 3/1974 | Feldman | |
| 4,010,744 | A | 3/1977 | Boyen | |
| 4,198,964 | A | 4/1980 | Honneffer | |
| 4,383,524 | A | 5/1983 | Boger | |
| 4,539,979 | A | 9/1985 | Bremer | |
| 4,541,421 | A | 9/1985 | Iversen et al. | |
| 4,662,366 | A | 5/1987 | Tari | |
| 4,674,483 | A | 6/1987 | Frederick | |
| 5,342,290 | A | 8/1994 | Schuellein | |
| 5,370,605 | A | 12/1994 | Weed | |
| 5,549,121 | A | 8/1996 | Vinci | |
| 5,788,659 | A | 8/1998 | Haas | |
| 5,865,780 | A | 2/1999 | Tuite | |
| 5,875,781 | A | 3/1999 | Klaus | |
| 6,708,693 | B1 | 3/2004 | Choy et al. | |
| 6,796,953 | B2 * | 9/2004 | Aduana, Jr. | A61F 5/04 |
| | | | | 602/32 |
| 2010/0071128 | A1 | 4/2010 | Campagna et al. | |
| 2010/0275377 | A1 | 11/2010 | West | |

* cited by examiner

DEVICES FOR APPLYING TENSION TO A PATIENT SHOULDER AND ASSOCIATED INSTALLATION METHOD

CROSS-REFERENCE TO RELATED APPLICATIONS

The present application is a U.S. national stage application claiming the benefit of International Application No. PCT/CA2012/000839, filed on Sep. 7, 2012, which claims priority from U.S. Provisional Patent Application No. 61/531,670, filed Sep. 7, 2011, the entire contents of which are incorporated herein by reference in their entirety.

PRIORITY STATEMENT UNDER 35 U.S.C § 119 (e) & 37 C.F.R. § 1.78

This non-provisional patent application claims priority based upon the prior U.S. provisional patent applications entitled "Upper limb positioner", application No. 61/531,670, filed Sep. 7, 2011, in the names of Jean-Marc MACTHIONG, Stefan PARENT, Hubert LABELLE, Mark DRISCOLL.

TECHNICAL FIELD

The present invention relates to a medical device and, more specifically, to a medical device that facilitates imaging of the neck region.

BACKGROUND

During any procedure or imaging of the neck region, it is important to properly clear the neck to allow adequate access and visualization. In particular, the shoulders can prevent adequate access and visualization of the neck region. As a working example, during anterior and posterior surgery in the neck region, frequent imaging of the cervical anatomical structures is required to assess the status of a surgeon's work. This necessitates unobstructed imaging of the cervical spine. A patient's shoulders neutral position is in lateral alignment with the caudal part of the neck region and, thus, will often obstruct the view of the cervical spine acquired from cross-table lateral imaging.

The present invention provides at least a partial solution to the identified problem.

SUMMARY

The present invention aims at providing a device and an installation method of the device. In use, the device of the present invention provides, among others, the exemplary advantage of moving an arm cover closed over a patient's arm together with the patient shoulder. The present invention may further provide at least some of the following exemplary advantages, e.g., a device that is less error-prone, simpler and quicker to use, more accommodating to hospital beds, configured to allow personnel position more proximately to patient, installed requiring less patient position adjustment, more compatible with, and less hampered by, any matter related to the clinical/surgical environment, more easily adjustable intra-operatively, more secured, arranged to avoid compression of the patient's chest, constructed not to impede patient respiration, more adjustable to accommodate all patient sizes, less expensive, and more effective in accomplishing its intended use.

A first aspect of the present invention is directed to a method for installing a device on an immobilised patient lying on a table. The method comprises (a) positioning an arm cover under the patient's arm and a shoulder strap connected to the arm cover under the patient's shoulder, (b) closing the arm cover over the patient's arm and (c) attaching the shoulder strap, over the patient's shoulder, to the closed arm cover. The method also further comprises (d) fixing an end of a longitudinal strap, connected to the arm cover, to the table opposite to the patient's head and (e) pulling on the longitudinal strap to apply tension on the shoulder strap, whereby the arm cover.

For greater certainty, in the context of the present invention, an immobilized patient is meant to be construed as a patient that is unlikely to slide on the table while tension is applied on the shoulder strap. Likewise, the relative term such as "under" or "over" are used to increase clarity of the text and not to limit the use of the device.

Optionally, the arm cover may present a surface that is suitable as a hook portion of a hook and loop fastener and further comprise at least one hook portion. Likewise the shoulder strap may comprise at least one hook portion. The method may then comprise applying localised pressure over at least one of the hook portion.

Optionally, the method may comprise repeating steps (a) to (c) for the patient's second arm before performing steps (d) and (e) and repeating steps (d) and (e) for the patient's second arm. A step of installing at least one transverse strip for maintaining a maximum distance between arm covers may optionally be performed. Installing the transverse strip may further comprise installing a first transverse strip in the back of the patient at neck height between the shoulder straps, a second transverse strip at torso height between the shoulder straps and a third transverse strip at abdomen height between the arm covers.

The longitudinal strap may comprise a tension lock for maintaining the tension in the longitudinal strap. Closing the arm cover may further comprise fixing a hook portion of a base strap over the closed arm cover, wherein the base strap extends from the longitudinal strap between the tension lock and the arm cover. The method may also comprise reducing the tension in the shoulder strap through the tension lock (e.g., for shortening or lengthening the longitudinal strap thereby adjusting tension in a controlled manner).

A second aspect of the present invention is directed to a device to be installed on an immobilised patient lying on a table. The device comprises an arm cover adapted to be positioned under a patient's arm before being closed thereover, a shoulder strap adapted to be positioned under the patient's shoulder and adapted to wrap the patient's shoulder when the shoulder strap is attached, over the patients shoulder, to the closed arm cover and a longitudinal strap adapted to be positioned along the patient and to be fixed to the table opposite to the patient's head. The longitudinal strap is capable of applying tension on the shoulder strap when shortened.

The shoulder strap may be unitary with the arm cover and extend therefrom, the longitudinal strap being attached to the arm cover.

The arm cover may present a surface that is suitable as a hook portion of a hook and loop fastener and further comprises at least one hook portion. Likewise, the shoulder strap may comprises at least one hook portion of a hook and loop fastener that is adapted to attach to the arm cover.

The longitudinal strap may comprise a tension lock for maintaining the tension in the longitudinal strap.

The device may also comprise a base strap that extends from the longitudinal strap between the tension lock and the arm cover and comprises a hook portion.

A third aspect of the present invention is directed to a device to be installed on an immobilised patient lying on a table. The device comprises an arm covering that comprises a shoulder strip to enclose a patient's shoulder, a tension strap connected to or enclosed within the arm covering. Tightening the tension strap length between the shoulder and a fixation of the tension strap to the table exerts tension on the patient's shoulder.

A fourth aspect of the present invention is directed to a kit comprising a first device as described in relation to the second or third aspect of the present invention that is adapted to fit a patient's right side, a second device as described in relation to the second or third aspect of the present invention that is adapted to fit a patient's left side and at least one transverse strip adapted to maintain a maximum distance between installed arm covers upon installation. Each end of the transverse strip may further comprise a hook portion of a hook and loop fastener.

BRIEF DESCRIPTION OF THE DRAWINGS

Further features and exemplary advantages of the present invention will become apparent from the following detailed description, taken in conjunction with the appended drawings, in which.

DETAILED DESCRIPTION

The present invention relates to an upper limb positioner to urge a patient's shoulders caudally and locate their arms while supine or prone on a medical table.

Medical tables (e.g., surgical or examination tables) often do not adequately provide support of the patient's arms. A need was identified to force a patient's shoulders caudally to improve visualization of the neck region while restraining the position of the patient's arms. Such clinical shortcomings, related to patient upper limb positioning, concern surgeries, injections, radiotherapy, imaging, etc.

Improved cervical visualization may be attempted by means of applying adhesive tape directly to the patient's shoulders, pulling the tape caudally, and fixing it to the medical table. This method, however, provides different disadvantages since it may insufficiently draw shoulders caudally, leave adhesive residue on the patient, may results in tape burn, endangers EKG leads, could lead to occluded intravenous (IVs) or arterial lines, and does not allow varying the pulling force without modifying the whole setup. In addition, in order to prepare the patient in the context of this method, an assistant needs to pull on the patient's wrist, either directly or via wrist straps, while potentially being positioned under a sterile surgical environment. Inconsistent tension on the shoulders during the radiograph is likely achieved by the present method. In addition, it is inconvenient during recurrent radiographs, may extend surgery time, may expose the assistant to radiation, may lead to injury (nerve and ligament), can block IV and arterial lines, and may jeopardize the sterile environment. Alternatively, use of different positions of the arms (e.g. swimmers position) could be used to better visualize the lower cervical spine, but the arm position is cumbersome and the visualization remains limited.

Alternatively, standard positioning of a patient's arms may be achieved by utilizing a multi-axis arm positioner that is fixed to the table supporting the patient's body. Although effective in supporting the patient's arms, this method requires significant lateral space and likely distances the personnel working position from the patient. The multi-axis arm positioner can also be displaced by the personnel during the procedure, and does not guarantee that the patient's arms will remain in their desired position. Moreover, the IVs are unsystematically found in the surgeon's working field. Alternatively, a patient's arms may be supported in their standard anatomical location (i.e., adjacent to body) via a blanket type materials rolled around the arms and maintained under the patient. This method is crude, difficult to adjust, unaccommodating to patient IVs, and requires significant fiddling to obtain secured positioning. In addition, this method precludes easy access to the arms when needed.

In accordance with one embodiment of the invention, the upper limb positioner causes the patient's shoulders to be drawn caudally to allow for accurate visualization and access to the neck region and to safely locate the arms adjacent to the patient's body. The device consists of partially or totally padded straps which enclose the patient's shoulders and are attached to a segment of the hospital table. These straps span longitudinally along the patient and are mated to itself using an adjustable buckle, a hook and loop fixation, and/or any adjustable fixation device. Caudal tension is achieved by tightening the strap through the adjustable buckle or adjustable fixation device. Conversely, loosening may be achieved through manually releasing the buckle and reducing strap tension or pulling an additional buckle, placed in series with the tension buckle, thus causing lengthening of the strap. The inner portions of the straps around the shoulders of the patient may contain a padded lining for comfort or to increase the contact surface with the shoulders. The outer portions of the straps may be covered with male VELCRO® (hooks). The outer portion of both straps may be linked transversely across the patient via female VELCRO® (loops) fasteners both ventral and dorsal to the patient to effectively secure the straps over the patient's shoulders while avoiding lateral travel, an action inherently caused by the increased slope angle from the shoulders to the axilla occurring when place under caudal tension. Alternatively, the transverse link may be achieved via a strap(s), including an adjustable buckle or connection, which may be moved cranially or caudally along the longitudinal straps. The patient's thorax, abdomen, and pelvis are maintained free to allow easy access if needed.

The adjoining upper limb harness is united to the shoulder straps by a plurality of female VELCRO® found on the outer material of the harness. The female VELCRO® strips found on the harness are configured to allow the arm position to be adjusted as desired. An upper limb harness failsafe cross-link strap may also be provided to offer a solid custom fixation of both upper limb harnesses to prevent lateral traveling of the arms. This optional connecting harness strap contains an adjustable buckle for quick and easy installation and to allow for additional adjustments of the medial/lateral location of the arms. The superior portion of the upper limb harness contains a void to allow IV, arterial and monitoring connections to pass freely. The inferior portion of the upper limb harness contains an adjoining male and female VELCRO® fixture, free from the shoulder straps, to allow easy opening of the harness to perform verifications and/or modifications to the IV, arterial and monitoring devices, and to the arm position. All attachments and connections of the upper limb positioner may be achieved via any adjoining methods such as snaps, buttons, zippers, hooks, ties, etc., or any combination thereof.

In accordance with another embodiment of the invention, the upper limb positioner causes the patient's shoulders to be drawn caudally to allow for accurate visualization and access to the neck region, and to comfortably locate the arms adjacent to the patient body. The device consists of upper limb coverings that open longitudinally along its length, straps, buckles, and hoop and loop fixations. The upper limb coverings pass over the patient's shoulders and conceal the majority of the patient's upper limbs from shoulders to hands. The opening is found medially and allows for the well-ordered inclusion or exclusion of the IV, arterial and monitoring devices within its construct. Closure of the upper limb covering is achieved via hoop and loop type or any other fixations. The coverings of both arms are joined transversely via another hoop and loop or any fixation method which, as in the other embodiment, may be installed at the desired location of the surgeon to avoid breast, abdominal, and/or genital compression and impediment of patient respiration. This transverse fixation also allows for arm position to be varied distal, proximal, palmar, and/or dorsal as desired. Connected to or enclosed within the arm coverings are tension straps that transmit caudal forces to the patient's shoulders. This tension force is achieved by tightening the strap length between the shoulder and the fixation to the hospital bed. Conversely, loosening may be achieved through manually releasing the buckle and reducing strap tension or pulling an additional buckle, placed in series with the tension buckle, thus causing lengthening of the strap.

In accordance with yet another embodiment of the invention, the upper limb positioner causes the patient's shoulders to be drawn caudally to allow for accurate visualization and access to the neck region and to comfortably locate the arms adjacent to the patient body. The device consists of an upper body covering, straps, and buckles. The upper body covering encloses the patient's upper limbs and torso in a manner that maintains the upper limbs adjacent to the patient's body. This upper body covering is placed under and then folded over the patient. Straps, connected to the bottom to or included within the covering are fixed to the hospital table. Caudal forces are transferred to the shoulders by shortening the strap length between the patient and the hospital table by means of an adjustable buckle or webbing clip. Conversely, loosening may be achieved through manually releasing the buckle and reducing strap tension or pulling an additional buckle, placed in series with the tension buckle, thus causing lengthening of the strap.

In accordance with yet another embodiment of the invention, the upper limb positioner causes the patient's shoulders to be drawn caudally to allow for accurate visualization and access to the neck region and to comfortably locate the arms adjacent to the patient body. The device consists of shoulder strips combined with arm coverings, buckles, and straps. The shoulder strips and arm coverings are unitary in construction and made from a padded material with loop characteristics (hook sensitive) such as but not limited to Veltex® or Velfoam®. The shoulder strips enclose the patient's shoulders. The connected arm coverings enclosed the patient's arms. Both the shoulder strips and arm coverings are interconnected through a variety of fixtures. Caudal forces are transferred to the shoulders by shortening the strap length between the patient and the hospital table by means of an adjustable buckle or webbing clip. Conversely, loosening may be achieved through manually releasing the buckle and reducing strap tension or pulling an additional buckle, placed in series with the tension buckle, thus causing lengthening of the strap.

In accordance with yet another embodiment of the invention, the upper limb positioner causes the patient's shoulders to be drawn caudally to allow for accurate visualization and access to the neck region and to comfortably locate the arms adjacent to the patient body. A unitary or combining receiving structure(s) is placed under or adjacent to the patient and encloses their shoulders and arms. This structure is open ended and allows personnel to visualize the entire upper body of the patient while the upper limb perimeter is closed for custom positioning. The perimeter upper limb positioner is adjustable to fit all patient sizes and to allow for upper limb position to be adjusted and maintained as desired. The upper limb positioner is maintained to the hospital table via a fixation or weight of the patient. As an example, in this embodiment, the upper limb positioner may be constructed in two separate pieces longitudinally split along its center line. The underside, that is to be in contact with the hospital table, may be a non-skid surface or a one-way one skid surface. This would allow for the displacement of the upper limb positioner and adjacent upper limbs to the desired location while the patient's weight provides the normal force for friction between the underside of the upper limb positioner and the hospital table to securely maintain their newly chosen position. Alternatively, if fixed to the hospital table, the position upper limb positioner and adjacent upper limbs may be adjusted via adjustable cranks. Alternatively, the upper limb positioner may be made from a series of connecting pieces that may be interlocked with each other via one way locking mechanism.

Figure 1:
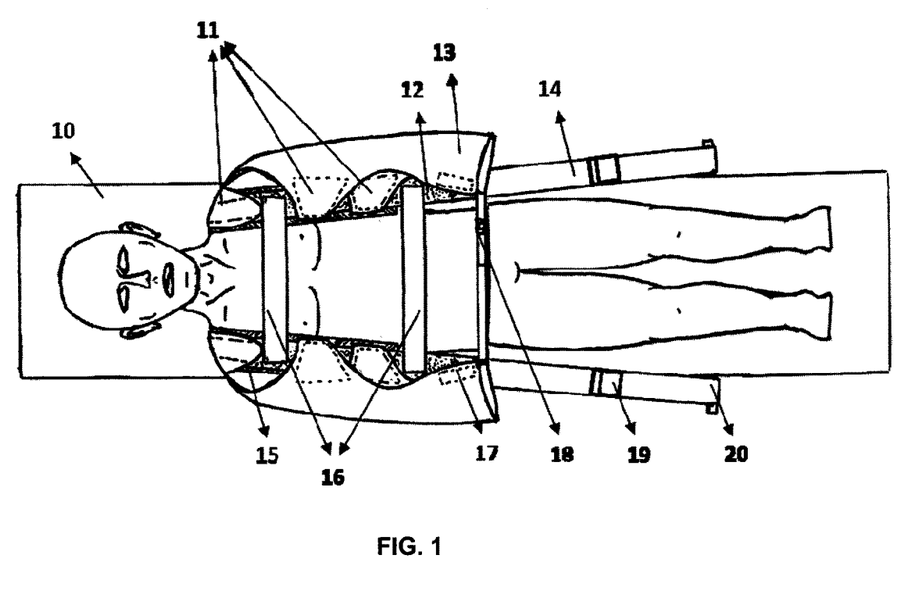
FIG. 1 is a top view of a patient on a hospital table featuring an upper limb positioner in accordance with the teachings of the present invention.
Figure 2:
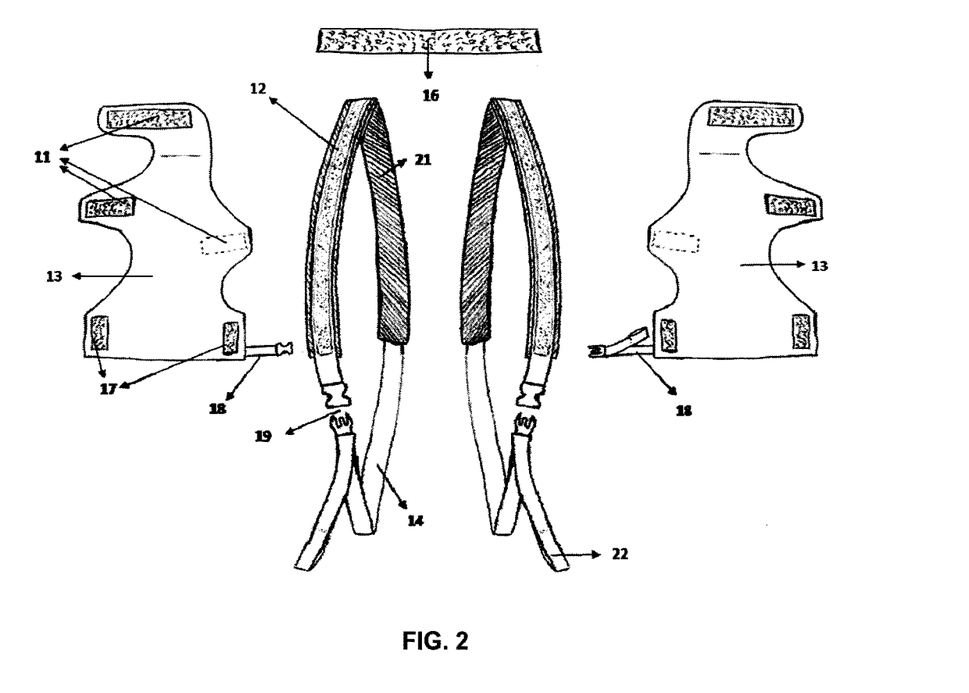
FIG. 2 is an exploded view of an upper limb positioner in accordance with the teachings of the present invention.

Reference is now made to the drawings, in which FIG. 1 and FIG. 2 show a patient lying supine on a hospital bed 10 and using an upper arm positioner in accordance with the teachings of the present invention. One end of the straps 14 enclose the patient's upper limbs, with the partially padded section of the straps 15 placed over the shoulders, while the other end fixes to the hospital table 20 via a simple enclosure fixation. Transverse linking straps 16, made from female VELCRO®, are positioned at the discretion of the operator to link both straps. The positions of the transverse linking straps are made to accommodate any patient while avoiding breast and chest compressions. The adjoining upper limb harnesses 13 are combined to the straps 14 by means of female VELCRO® 11 over the shoulders and a number of other locations on the straps 14 to the effectively secure the upper limb harness 13, thus forming the upper limb positioner. The inferior portion of the upper limb harness, near the patients hands, may be joined to itself also using hook and loop methods for an inter-linking fixation 17. This, sub-fixation allows the patient's arms and corresponding IVs to be easily verified and adjusted as needed. A failsafe crosslink 18 joins both upper limb harnesses for assured positioning of the arms via an adjustable buckle. At any moment during the installation of the upper limb positioner or intra-operatively, the shoulders may be forced caudally by reducing the length of the strap 14 between the patient's shoulders and the fixation to the hospital bed 20 via the adjustable buckle 19. To permit easy intra-operative adjustments, a pull strap 22 is offered that extends below the surgical sterile environment. As needed, this pull strap may be accessed and pulled to additionally urge the patient's shoulders caudally.

Figure 3:
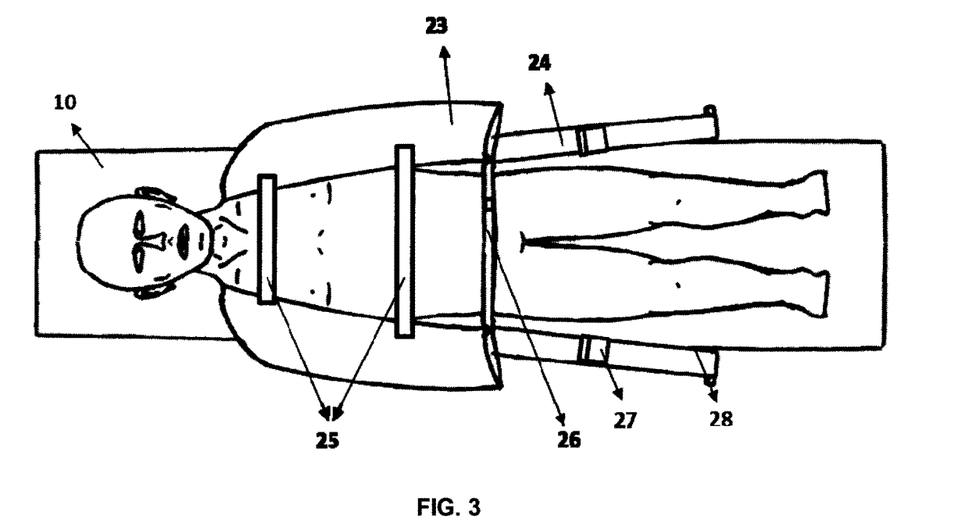
FIG. 3 is a top view of a patient on a hospital table featuring an upper limb positioner in accordance with the teachings of the present invention.

In reference to FIG. 3 the patient is lying supine on a hospital bed 10 fitted with another embodiment of the applicants' invention, the upper arm positioner. One end of the strap 24 is fixed to or may be included within the upper limb harness 23 while the other end fixes to the hospital table 28 via a simple enclosure fixation. Transverse linking straps 25, made from female VELCRO®, are positioned at the discretion of the operator to link both upper limb harnesses. The positions of the transverse linking straps are made to accommodate any patient while avoiding breast and chest compressions. As in the previous embodiment, the inferior portion of the upper limb harness, near the patients hands, may be joined to itself also using hook and loop methods for an inter-linking fixation. This, sub-fixation allows the patient's arms and corresponding IVs to be easily verified and adjusted as needed. A failsafe crosslink 26 joins both upper limb harnesses for assured positioning of the arms via an adjustable buckle. At any moment during the installation of the upper limb positioner or intra-operatively, the shoulders may be forced caudally by reducing the length of the strap 24 between the patient's shoulders and the fixation to the hospital bed 28 via the adjustable buckle 27.

Figure 4:
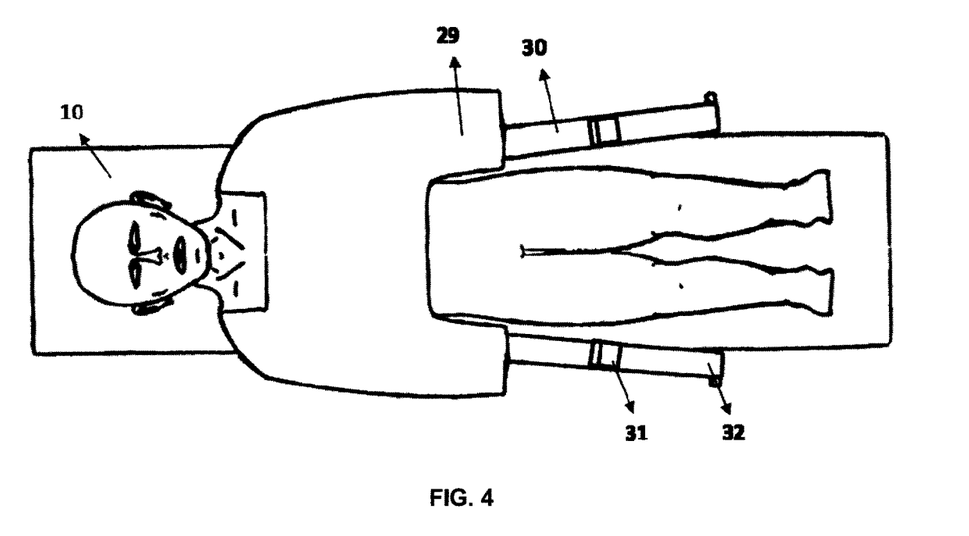
FIG. 4 is a top view of a patient on a hospital table featuring an upper limb positioner in accordance with the teachings of the present invention.

In reference to FIG. 4 the patient is lying supine on a hospital bed 10 fitted with yet another embodiment of the applicants' invention, the upper arm positioner. One end of the strap 30 is fixed to or may be included within the upper body harness 29 while the other end fixes to the hospital table 32 via a simple enclosure fixation. The upper body harness encloses the patient's upper body. This is achieved by laying the patient on the inferior portion of the upper body harness and then folding the upper portion over the patient. The lower and upper portions of the harness are combined using a plurality of hook and loop fixations found at the shoulder level and along its connecting portions. At any moment during the installation of the upper limb positioner or intra-operatively, the shoulders may be forced caudally by reducing the length of the strap 29 between the patient's shoulders and the fixation to the hospital bed 32 via the adjustable buckle 31.

Figure 5:
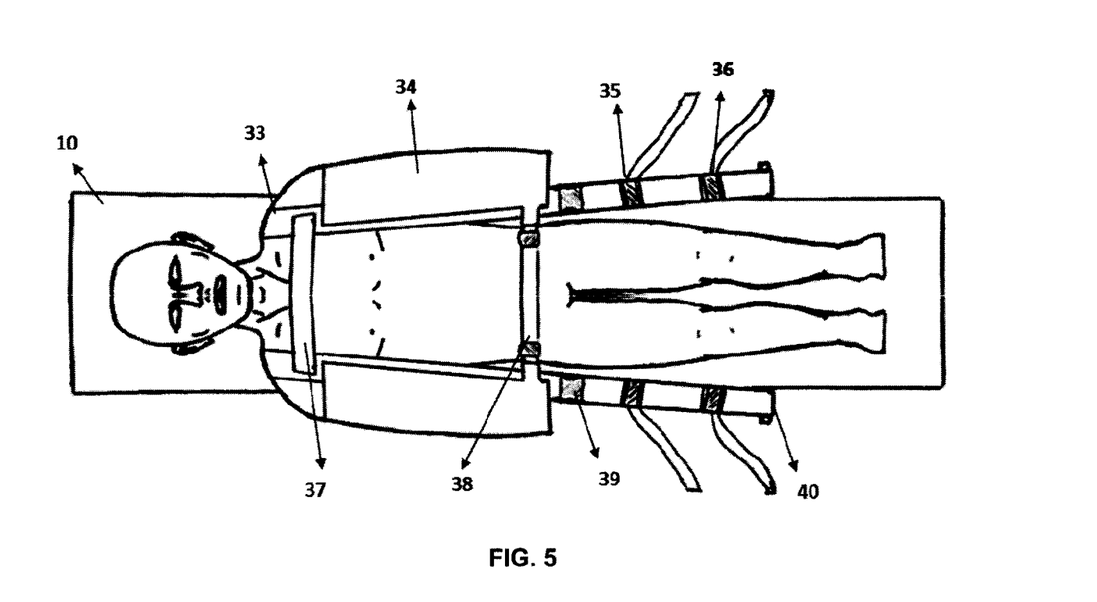
FIG. 5 is a top view of a patient on a hospital table featuring an upper limb positioner in accordance with the teachings of the present invention.
Figure 6:
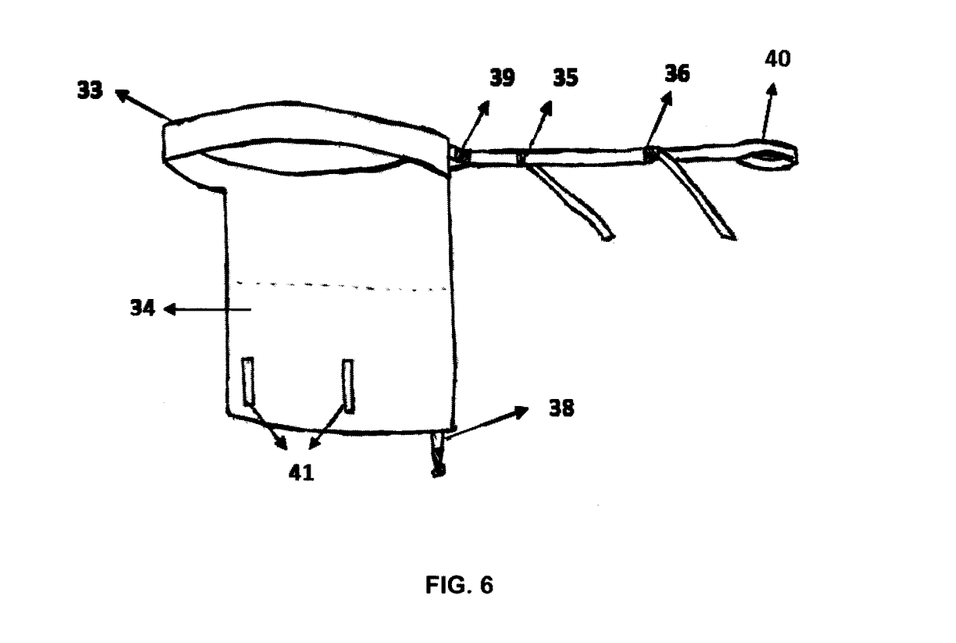
FIG. 6 is an exploded view of a portion an upper limb positioner in accordance with the teachings of the present invention.

In reference to FIG. 5 and FIG. 6 the patient is lying supine on a hospital bed 10 fitted with yet another embodiment of the applicants' invention, the upper arm positioner. First, the shoulder strips 33 are positioned over the patient's shoulders and connected to itself via a fixation such as a buckle 39. Second, the arm coverings 34 are anteriorly folded over the patient's arms and connected to the shoulder strips 33 via a hook and loop fixation(s) 41. A transverse safety connection 38 of the arm coverings is provided and consists of a strap with a buckle(s) connection. This connection secures the arm position, allows fine tuning of arm position, and grants easy access to the patient's IVs and arterial lines. Transverse linking strap(s) 37, possibly made from a combination of Veltex® and Velcro®, are positioned at the discretion of the operator to link both shoulder strips and avoid lateral migration of the upper limb positioner. The positions of the transverse linking straps are made to accommodate any patient while avoiding breast and chest compressions. At any moment during the installation of the upper limb positioner or intra-operatively, the shoulders may be forced caudally by reducing the length of the strap between the patient's shoulders and the fixation to the hospital bed 40 via the adjustable buckle 36. Conversely, loosening may be achieved through manually releasing the buckle and reducing strap tension or pulling an additional buckle 35, placed in series with the tension buckle, thus causing lengthening of the strap.

Figure 7:
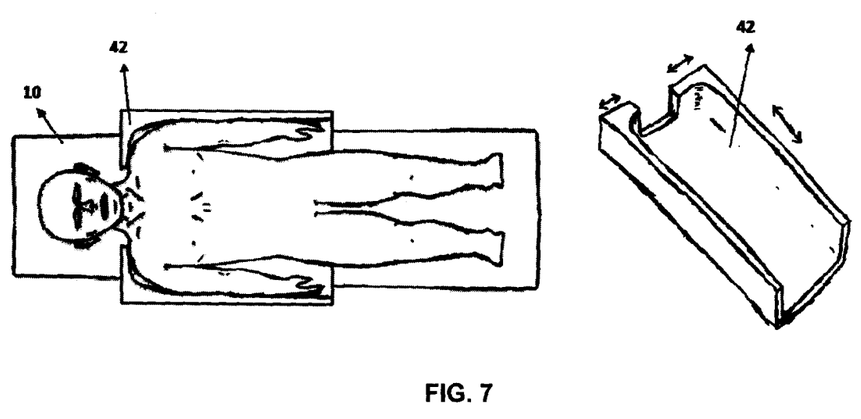
FIG. 7 is a top view of a patient on a hospital table featuring an upper limb positioner in accordance with the teachings of the present invention and a perspective view of an upper limb positioner in accordance with the teachings of the present invention.

In reference to FIG. 7, the patient is lying supine on a hospital bed 10 fitted with yet another embodiment of the applicants' invention, the upper arm positioner. The patient's upper limbs, from shoulders to hands, are enclosed and supporter by the upper limb positioner 42. The upper limb positioner 42 may be placed before or after the patient is laid on the hospital table. Once installed, position of the patient's upper limbs may be moved and maintained as desired by displacing the position of the upper limb positioner. In turn, the upper limb positioner's location is secured via friction, fixations to the hospital bed, and/or inter-locking mechanisms between respective pieces.

Figure 8:
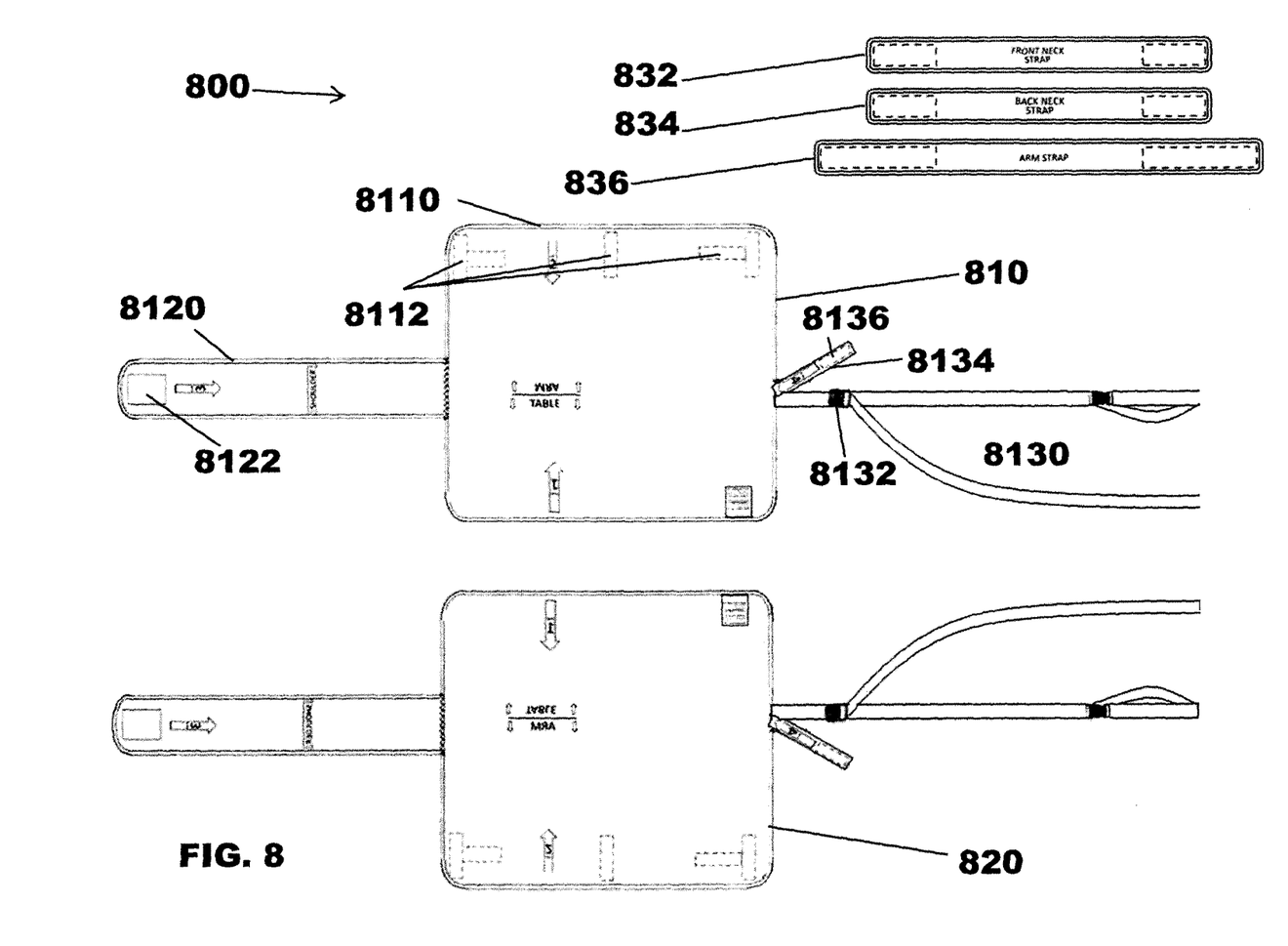
FIG. 8 is a schematic representation of an exemplary kit in accordance with the teachings of the present invention.

FIG. 8 shows an exemplary kit 800 in accordance with the teachings of the present invention. The kit 800 comprises a first device 810 adapted to fit under a patient's left arm The first device 810 comprises an arm cover 8110 adapted to be positioned under a patient's arm before being closed thereover. The first device 810 also comprises a shoulder strap 8120 adapted to be positioned under the patient's shoulder. The shoulder strap 8120 is further adapted to wrap the patient's shoulder when the shoulder strap is attached, over the patient's shoulder, to the closed arm cover 8110. The first device 810 further comprises a longitudinal strap 8130 adapted to be positioned along the patient and to be fixed to the table opposite to the patient's head. The longitudinal strap 8130 is capable of applying tension on the shoulder strap when shortened. In the exemplary kit 800, the first device 810 presents, as an example, the shoulder strap 8120 being unitary with the arm cover 8110 and extending therefrom and further presents the longitudinal strap 8130 being attached to the arm cover 8110.

The arm cover 8110 may further present a surface that is suitable as a hook portion of a hook and loop fastener and further comprise at least one hook portion 8112. Likewise, the shoulder strap 8120 may comprise at least one hook portion 8122 of a hook and loop fastener. The longitudinal strap 8130 may also comprise a tension lock 8132 for maintaining the tension in the longitudinal strap 8130. A base strap 8134 may also further extend from the longitudinal strap 8130 between the tension lock 8132 and the arm cover 8110 and comprise a hook portion 8136.

As skilled reader will appreciate, the end of the longitudinal strap 8130 that is not attached or otherwise connected to the arm cover 8110 is meant to be pulled, once the device is properly installed, to increase tension is the longitudinal strap 8130 which, in turn, increases tension applied to the patient's shoulder. Skilled person will notice that the pulled end of the longitudinal strap 8130 that extends from the tension lock 8132 is thereby unlikely to extend in an eventual sterile field (e.g., required during a surgery). The arrangement of the device 810 makes it possible to adjust the tension in the longitudinal strap 8130 while limiting the risk of jeopardizing the eventual sterile field.

The kit 800 also comprises a second device 820 adapted to fit under a patient's right arm. In the exemplary kit 800, both devices 810 and 820 have identical mirrored features. Skilled readers will understand that other kits could be provided with different devices adapted to fit different context of use.

The kit 800 also comprises at least one transverse strip (832, 834, 836) adapted to maintain a maximum distance between the arm covers of the first device 810 and second device 820, once installed. Each end of each transverse strip (832, 834, 836) may also comprise a hook portion of a hook and loop fastener.

Figure 9:
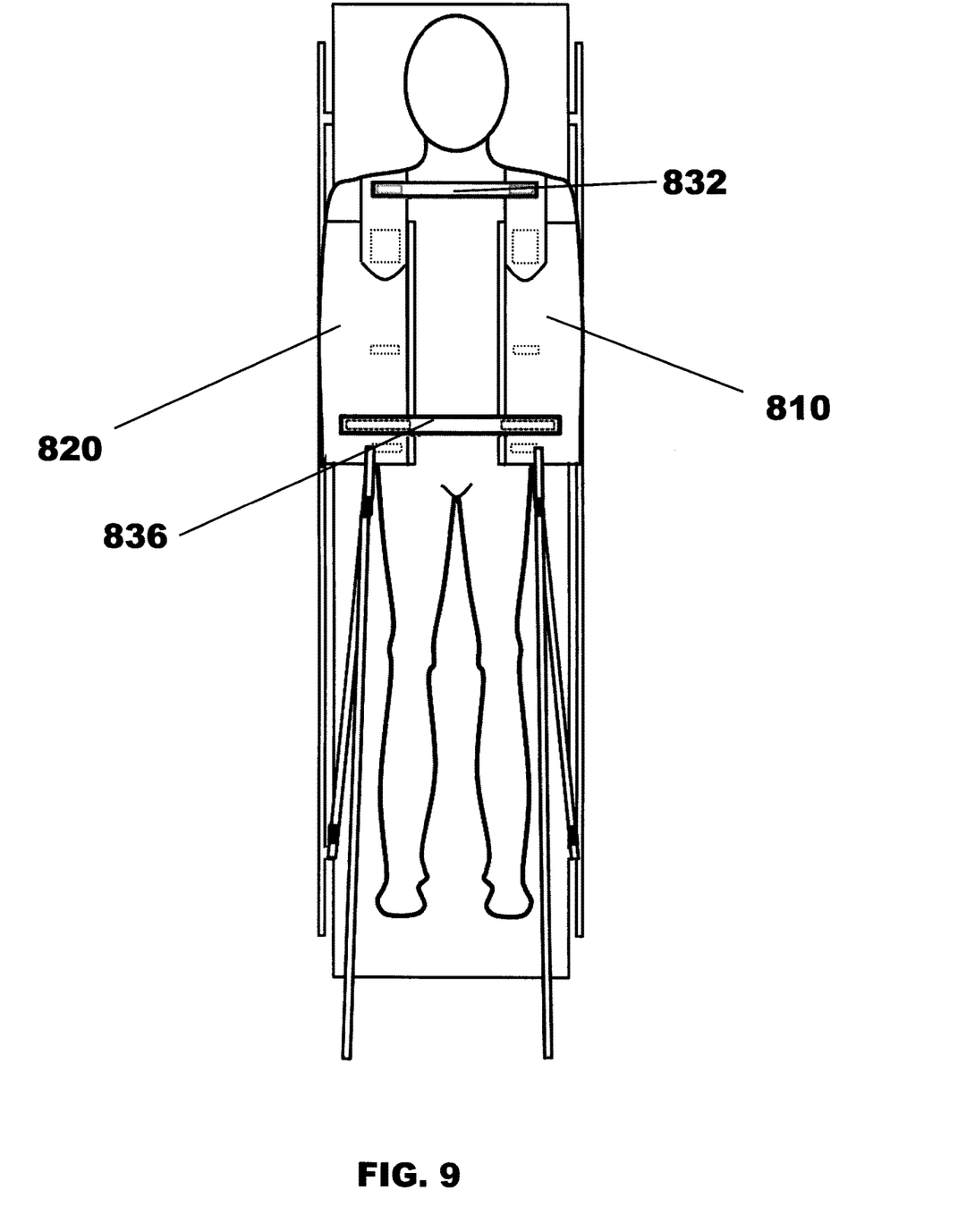
FIG. 9 is a top view of a patient on a hospital table featuring at least some of the parts of the exemplary kit of FIG. 8.

FIG. 9 shows a top view of the exemplary kit 800 once installed on a patient. In the example of FIG. 9, transverse strips 832 and 836 are visible while transverse strip would be installed under the patient.

Figure 10:
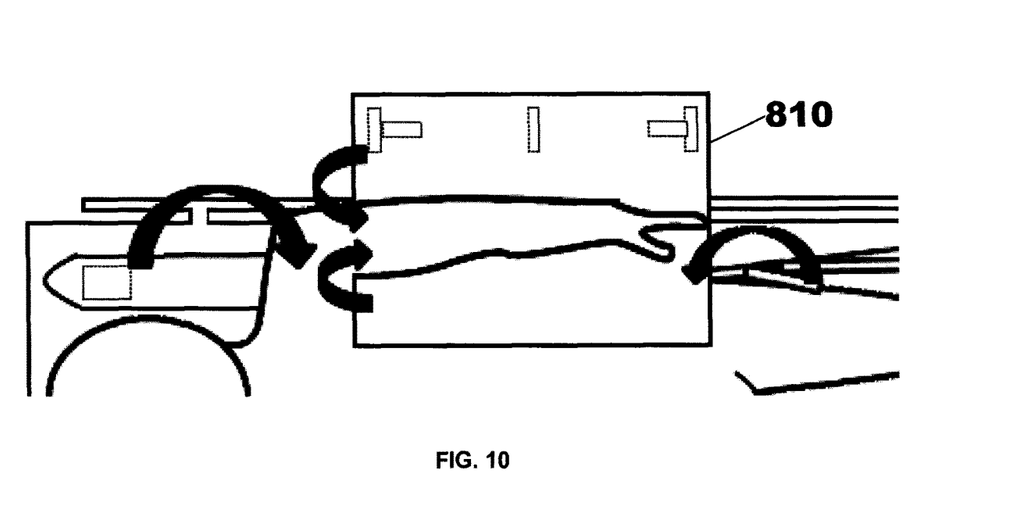
FIG. 10 is an exemplary representation of installation in accordance with the teachings of the present invention.
Figure 11:
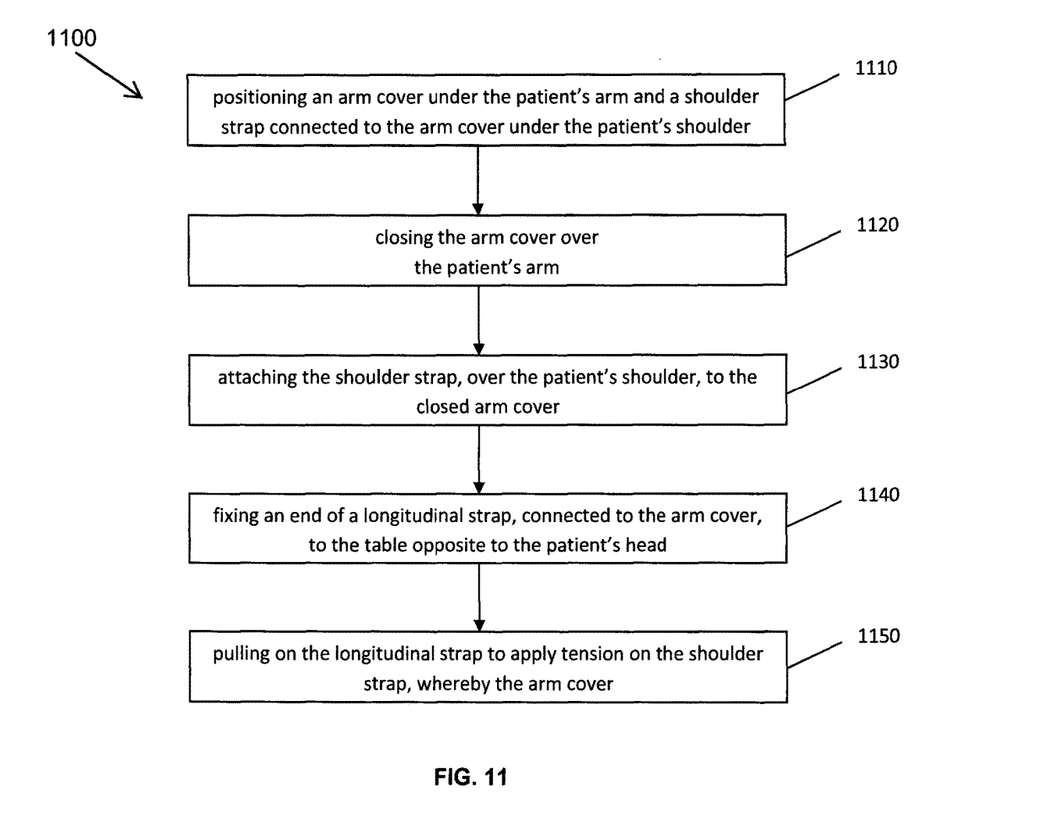
FIG. 11 is a flow chart of an exemplary method of installation of a device in accordance with the teachings of the present invention.

Reference is now made concurrently to FIG. 10 and FIG. 11. FIG. 10 shows a top view of a patient during installation of the first device 810 of the exemplary kit 800. FIG. 11 shows a flow chart of an exemplary installation method 1100 of the first device 810. The patient is immobilized (not shown) and lying on a table.

The method comprises positioning 1110 an arm cover 8110 under the patient's arm and a shoulder strap 8120 connected to the arm cover 8110 under the patient's shoulder. The method then follows with closing 1120 the arm cover over the patient's arm and attaching 1130 the shoulder strap 8120, over the patient's shoulder, to the closed arm cover 8110. Thereafter, an end (not shown on FIG. 10) of a longitudinal strap 8130, connected to the arm cover 8110, is fixed 1140 to the table opposite to the patient's head. The method of installation follows with pulling 1150 on the longitudinal strap 8130 to apply tension on the shoulder strap 8120. As can be appreciated, any movement of the patient's shoulder along the tension will also cause an equivalent movement in the arm cover 8110.

Closing 1120 the arm cover 8110 may also further comprise fixing the hook portion 8136 of the base strap 8134 over the closed arm cover 8130. Reducing (not shown) the tension in the shoulder strap 8120 may be achieve through the tension lock 8132 (if present).

In the most common expected use of the present invention, the second device 820 of the exemplary kit 800 is installed at least before performing the step 1150 of pulling on the longitudinal strap 8130, an maybe before the step 1140 of fixing the longitudinal strap 8130 to the table. Steps 1110 to 1140 are repeated for the patient's second arm. The method may also comprise installing (not shown) at least one transverse strip (832, 834, 836) for maintaining a maximum distance between arm covers. For instance, a first transverse strip 834 may be installed in the back of the patient at neck height between the shoulder straps, a second transverse strip 832 may be installed at torso height between the shoulder straps and a third transverse strip 836 may be installed at abdomen height between the arm covers.

The method 1100 may also further comprise applying (now shown) localised pressure over at least some of the hook portions of the first device 810.

In the course of the above described embodiments, a number of alternatives have been identified and others may well occur to those skilled in the art without departing from the field of the invention. Thus, various combinations, sub-combinations, and sundry adaptations are maintained under the principles of the provided invention.

A method is generally conceived to be a self-consistent sequence of steps leading to a desired result. Skilled persons will readily understand how the steps of the exemplary methods described herein could be rearranged without affecting the desired result. Exemplary embodiments have been described to demonstrate the use, principles, and function of the invention disclosed herein. These descriptions and illustrations are non-limiting exemplary embodiments and no limitation to the scope of the invention is thereby intended. Any alteration or modification to the device or alternative application of the invention principles are contemplated to normally occur by those with ordinary skill in the art to which the invention relates. Likewise, the description of the present invention has been presented for purposes of illustration but is not intended to be exhaustive or limited to the disclosed embodiments. Many modifications and variations will be apparent to those of ordinary skill in the art. The embodiments were chosen to explain the principles of the invention and its practical applications and to enable others of ordinary skill in the art to understand the invention in order to implement various embodiments with various modifications as might be suited to other contemplated uses.

The invention claimed is:

1. A method for installing a device for applying tension to a shoulder of an immobilised patient lying on a table, the method comprising:
    (a) positioning an arm cover between the patient's arm and the table, the arm cover being configured to entirely cover the patient's arm when the arm cover is closed over the patient's arm, the arm cover comprising: a shoulder strap having a first end attached to an upper portion of the arm cover and an opposite second end extending from the arm cover, and a longitudinal strap having a first end attached to a bottom portion of the arm cover and an opposite second end extending therefrom in opposite direction relatively to the shoulder strap;
    (b) positioning the shoulder strap connected to the arm cover under the patient's shoulder;
    (c) closing the arm cover over the patient's arm;
    (d) wrapping the shoulder strap over the patient's shoulder and attaching the opposite second end of the shoulder strap to the closed arm cover;
    (e) fixing the opposite second end of the longitudinal strap to the table opposite to the patient's head near the patient's legs; and
    (f) pulling on the longitudinal strap to apply tension on the arm cover and subsequently on the shoulder strap, wherein augmenting the tension on the shoulder strap causes the patient's shoulder to move away from the patient's neck while avoiding longitudinal tension to the patient's wrist and elbow.

2. The method of claim 1, wherein the arm cover presents a surface that is suitable as a loop portion of a hook and loop fastener and further comprises at least one hook portion, wherein closing the arm cover further comprises applying localised pressure over at least one of the hook portion.

3. The method of claim 2 further comprising repeating steps (a) to (d) for the patient's second arm before performing steps (e) and (f) and repeating steps (e) and (f) for the patient's second arm, wherein the method further comprises, before performing step (f), installing at least one transverse strip for maintaining a distance that will not increase between arm covers, wherein each end of the at least one transverse strip comprises a hook portion of a hook and loop fastener and wherein installing the transverse strip further comprises applying localised pressure over the hook portion of the transverse strip.

4. The method of claim 3, wherein the shoulder strap presents a surface that is suitable as a loop portion of a hook and loop fastener and wherein installing the at least one transverse strip comprises installing a first transverse strip between the shoulder straps and a second transverse strip between the arm covers.

5. The method of claim 2, wherein the shoulder strap comprises at least one hook portion of a hook and loop fastener and wherein attaching the shoulder strap to the closed arm cover further comprises applying localised pressure over the hook portion of the shoulder strap.

6. The method of claim 1, wherein the longitudinal strap comprises a tension lock for maintaining the tension in the longitudinal strap.

7. The method of claim 6, wherein pulling the longitudinal strap is performed by pulling on the end of the longitudinal strap that extends from the tension lock and is not fixed to the table.

8. The method of claim 1 further comprising repeating steps (a) to (d) for the patient's second arm before performing steps (e) and (f) and repeating steps (e) and (f) for the patient's second arm, wherein the method further comprises, before performing step (f), installing at least one transverse strip for maintaining a distance that will not increase between arm covers.

9. A device for applying tension to shoulders of an immobilised patient lying on a table, the device comprising:
(a) a first arm cover configured to entirely cover a patient's left arm when the first arm cover is closed over the patient's left arm, the first arm cover comprising a first shoulder strap having a first end attached to an upper portion of the first arm cover and an opposite second end extending from the first arm cover, the first shoulder strap being configured to enclose a patient's left shoulder when the opposite second end is attached to the first arm cover;
(b) a second arm cover configured to entirely cover a patient's right arm when the second arm cover is closed over the patient's right arm, the second arm cover comprising a second shoulder strap having a first end attached to an upper portion of the second arm cover and an opposite second end extending from the second arm cover, the second shoulder strap being configured to enclose a patient's right shoulder when the opposite second end is attached to the second arm cover;
(c) a first tension strap connected to or enclosed within the first arm cover, the first tension strap having a first end attached to a bottom portion of the first arm cover and an opposite second end extending therefrom in opposite direction relatively to the first shoulder strap, wherein tightening the first tension strap length between the first end attached to the bottom portion of the first arm cover and a fixation of the first tension strap to the table exerts tension on the first arm cover and subsequently on the first shoulder strap configured to enclose the patient's left shoulder;
(d) a second tension strap connected to or enclosed within the second arm cover, the second tension strap having a first end attached to a bottom portion of the second arm cover and an opposite second end extending therefrom in opposite direction relatively to the second shoulder strap, wherein tightening the second tension strap length between the first end attached to the bottom portion of the second arm cover and a fixation of the second tension strap to the table exerts tension on the second arm cover and subsequently on the second shoulder strap configured to enclose the patient's right shoulder;
(e) at least one tension lock for maintaining the tension in the first and the second tension straps, wherein augmenting the tension on the first shoulder strap once installed causes the patient's left shoulder to move away from the patient's neck while avoiding longitudinal tension to the patient's left wrist and elbow and wherein augmenting the tension on the second shoulder strap stray once installed causes the patient's right shoulder to move away from the patient's neck while avoiding longitudinal tension to the patient's right wrist and elbow; and
(f) at least one transverse strip adapted to maintain a maximum distance between the first and second arm covers once installed.

10. The device of claim 9, wherein the first and second arm coverings present a surface that is suitable as a loop portion of a hook and loop fastener and further comprises at least one hook portion.

11. The device of claim 10, wherein the first shoulder strip strap comprises at least one hook portion of a hook and loop fastener that is adapted to attach to the first arm cover and the second shoulder strap comprises at least one hook portion of a hook and loop fastener that is adapted to attach to the second arm cover.

12. The device of claim 9, wherein the first tension strap comprises a first tension lock from the at least one tension lock for maintaining the tension in the first tension strap and the second tension strap comprises a second tension lock from the at least one tension lock for maintaining the tension in the second tension strap.

13. The device of claim 12, wherein the end of the first and second tension straps that extends from the first and second tension locks, and is not adapted to be fixed to the table, is adapted to be pulled to apply tension in the first and second tension straps.

14. The device of claim 9, wherein the first shoulder strap is unitary with the first arm cover and wherein the second shoulder strap is unitary with the second arm cover.

15. The device of claim 9, wherein each end of the at least one transverse strip comprises a hook portion of a hook and loop fastener.

16. A device for applying tension to a shoulder of an immobilised patient lying on a table, the device comprising:
(a) an arm cover adapted to be positioned between a patient's arm and the table before being closed over the patient's arm, the arm cover being configured to entirely cover the patient's arm when the arm cover is closed over the patient's arm;
(b) a shoulder strap having a first end attached to an upper portion of the arm cover and on opposite second end extending from the arm cover, the shoulder strap being adapted to be positioned under the patient's shoulder and to be wrapped over the patient's shoulder when the opposite second end of the shoulder strap is attached to the closed arm cover; and (c) a longitudinal strap having a first end attached to a bottom portion of the arm cover and an opposite second end extending therefrom in opposite direction relatively to the shoulder strap, the longitudinal strap being adapted to be positioned along the patient and having the opposite second end to be fixed to the table opposite to the patient's head, wherein the longitudinal strap is capable of applying tension on the arm cover and subsequently on the shoulder strap when the longitudinal strap is shortened; and (d) a tension lock for maintaining the tension in the longitudinal strap, wherein augmenting the tension on the shoulder strap once installed causes the patient's shoulder to move away from the patient's neck while avoiding longitudinal tension to the patient's wrist and elbow.

17. The device of claim 16, wherein the arm cover presents a surface that is suitable as a loop portion of a hook and loop fastener and further comprises at least one hook portion.

18. The device of claim 17, wherein the shoulder strap comprises at least one hook portion of a hook and loop fastener that is adapted to attach to the arm cover.

19. The device of claim 16, wherein the longitudinal strap comprises the tension lock for maintaining the tension in the longitudinal strap.

20. The device of claim 19, wherein the end of the longitudinal strap that extends from the tension lock, and is not adapted to be fixed to the table, is adapted to be pulled to apply tension in the longitudinal strap.

21. The device of claim 16, wherein the first end of the shoulder strap is unitary with the arm cover.

22. A kit comprising:
(a) a first device comprising:
   (i) a first arm cover adapted to be positioned under a patient's left arm before being closed thereover, the first arm cover being configured to entirely cover the patient's left arm when the first arm cover is closed over the patient's left arm;
   (ii) a first shoulder strap having a first end attached to an upper portion of the first arm cover and an opposite second end extending from the first arm cover, the first shoulder strap being positioned under the patient's left shoulder and adapted to wrap the patient's left shoulder when the shoulder strap is attached, over the patient's left shoulder, to the closed first arm cover; and
   (iii) a first longitudinal strap having a first end attached to a bottom portion of the first arm cover and an opposite second end extending therefrom in opposite direction relatively to the first shoulder strap, the first longitudinal strap being adapted to be positioned along the patient and to be fixed to the table opposite to the patient's head, wherein the first longitudinal strap is capable of applying tension on the first arm cover and subsequently on the first shoulder strap when shortened;
   (iv) a first tension lock for maintaining the tension in the first longitudinal strap, wherein augmenting the tension on the first longitudinal strap once installed causes the patient's left shoulder to move away from the patient's neck while avoiding longitudinal tension to the patient's left wrist and elbow;
(b) a second device comprising:
   (i) a second arm cover adapted to be positioned under a patient's right arm before being closed thereover, the second arm cover being configured to entirely cover the patient's right arm when the second arm cover is closed over the patient's right arm;
   (ii) a second shoulder strap having a first end attached to an upper portion of the second arm cover and an opposite second end extending from the second arm cover, the second shoulder strap being positioned under the patient's right shoulder and adapted to wrap the patient's right shoulder when the shoulder strap is attached, over the patient's right shoulder, to the closed second arm cover; and
   (iii) a second longitudinal strap having a first end attached to a bottom portion of the second arm cover and an opposite second end extending therefrom in opposite direction relatively to the second shoulder strap, the second longitudinal strap being adapted to be positioned along the patient and to be fixed to the table opposite to the patient's head, wherein the second longitudinal strap is capable of applying tension on the second arm cover and subsequently on the second shoulder strap when shortened;
   (iv) a second tension lock for maintaining the tension in the second longitudinal strap, wherein augmenting the tension on the second longitudinal strap once installed causes the patient's right shoulder to move away from the patient's neck while avoiding longitudinal tension to the patient's right wrist and elbow; and
(c) at least one transverse strip adapted to maintain a maximum distance between the first and second arm covers once installed.

23. The kit of claim 22, wherein each end of the at least one transverse strip comprises a hook portion of a hook and loop fastener.

* * * * *